United States Patent
Mindala

(10) Patent No.: US 8,521,550 B2
(45) Date of Patent: Aug. 27, 2013

(54) SYSTEM AND METHOD FOR DETERMINING THE COST OF A PHARMACEUTICAL

(75) Inventor: James Mindala, Chagrin Falls, OH (US)

(73) Assignee: Envision Pharmaceutical Holdings, Inc., Twinsburg, OH (US)

(*) Notice: Subject to any disclaimer, the term of this patent is extended or adjusted under 35 U.S.C. 154(b) by 1747 days.

(21) Appl. No.: 10/316,024

(22) Filed: Dec. 11, 2002

(65) Prior Publication Data

US 2004/0117323 A1 Jun. 17, 2004

(51) Int. Cl.
*G06Q 50/00* (2012.01)
*G06Q 40/00* (2012.01)

(52) U.S. Cl.
USPC .................................. 705/2; 705/35

(58) Field of Classification Search
USPC ........................................................ 705/2
See application file for complete search history.

(56) References Cited

U.S. PATENT DOCUMENTS

| 6,272,472 | B1* | 8/2001 | Danneels et al. | 705/27 |
| 2001/0037216 | A1* | 11/2001 | Oscar et al. | 705/2 |
| 2002/0059317 | A1* | 5/2002 | Black et al. | 707/200 |
| 2002/0111832 | A1* | 8/2002 | Judge | 705/3 |

OTHER PUBLICATIONS

Morton, Fiona Scott, "The Strategic Response by Pharmaceutical Firms to the Medicaid Most-Favored-Customer Rules", Summer, 1997, The RAND Journal of Economics, vol. 28, No. 2., pp. 269-290.*
Danzon, Patricia M., "Reference Pricing: Theory and.Evidence", The Wharton School, University of Pennsylvania, May 22, 2001.*
Drug Topics, "Fixed Fee Violates Antitrust Laws, Pharmacists in Texas Charge", Sep. 15, 1977, vol. 121, Iss. 18, p. 9.*
Gencarelli, Dawn M., "Average Wholesale Price for Prescription Drugs: Is there a More Appropriate Pricing Mechanism", Jun. 7, 2002, NHPF Issue Brief, No. 775.*
Gencarelli, Dawn M., "Average Wholesale Price for Prescription Drugs: Is there a More Appropriate Pricing Mechanism", Jun. 7, 2002., NHPF Issue Brief, No. 775.00.*

* cited by examiner

*Primary Examiner* — Tran Nguyen

(74) *Attorney, Agent, or Firm* — Baker & Hostetler LLP

(57) ABSTRACT

A method for calculating a subscriber pharmaceutical cost that incorporates a discount is disclosed that includes receiving the discount from at least one of a pharmaceutical manufacturer and a pharmacy, and determining a subscriber cost that includes the discount, and that reduces the cost of the pharmaceutical to the subscriber at the point of sale.

33 Claims, 7 Drawing Sheets

FIG. 4

|  | Drug Type: | Cost Benefit |
|---|---|---|
| 96 — | Tier 1: Generic | Lowest Cost |
| 98 — | Tier 2: Primary Preferred Brand | Lowest Cost Brand |
| 100 — | Tier 3: Preferred Brand | Higher Cost Brand |
| 102 — | Tier 4: Selected Brand | Limited Cost Sharing |
| 104 — | Tier 5: Non-covered Brands | No discount or coverage-due to manufacturer failure to lower drug costs for the program |

FIG. 5

SYSTEM AND METHOD FOR DETERMINING THE COST OF A PHARMACEUTICAL

FIELD OF THE INVENTION

The present invention relates generally to health benefits. More particularly, the present invention is directed to a pharmacy benefit prescription drug program that passes for example, rebates, discounts, incentive fees, and/or administrative fees, provided by pharmaceutical manufacturers and pharmacies, to purchasers at the point of sale, and that directly deducts the rebates and/or discounts from an original cost of the pharmaceutical.

BACKGROUND OF THE INVENTION

The cost of pharmaceuticals/drugs has substantially increased in recent years. This directly affects the costs to health care insurance carriers or other insurers that offer prescription/pharmaceutical programs or benefits. To compensate for this, insurers typically raise the premiums that they charge their clients for the pharmaceutical benefits.

Employers, who represent a majority of an insurer's pharmaceutical benefit clients, purchase the benefits for the benefit of their current employees. To offset some of the cost borne by the employer for these benefits, a premium is often charged to the employee by the employer if the employee decides to subscribe to the pharmaceutical benefits.

When an insurer raises the price of the pharmaceutical benefits, the employer may also increase the employee's premium to avoid an increase in the cost of providing the pharmaceutical benefits. The employer may absorb the additional cost, however, absorption of the cost by the employer may lead to a reduction in profits, personnel layoffs, and/or reductions in health care benefits available to the employees. Further, an employer may fail to attract a potential employee if the cost of the pharmaceutical benefits, and the services associated with the pharmaceutical benefits, are less favorable than the cost and services related to pharmaceutical benefits offered by another potential employer.

A conventional method, utilized by employers to mitigate increased pharmaceutical benefit costs, is the multi-tier co-payment pharmaceutical benefits structure. The multi-tier co-payment pharmaceutical benefits structure is designed to pass increased costs to an employee/beneficiary. In the multi-tier co-payment pharmaceutical benefits structure, the employee/beneficiary of the pharmaceutical benefits pays a fixed co-payment for pharmaceuticals at the time of purchase.

The amount of the co-payment in the multi-tier structure will vary according to whether the pharmaceutical is, for example, a generic drug or a brand drug. The co-payment may also vary according to whether any discounts and/or rebates are offered by a pharmacy and/or pharmaceutical manufacturer for the specific pharmaceutical. By classifying the pharmaceuticals according to their costs and imposing higher co-payments for higher priced drugs, employers pass a greater portion of the prescription drug benefit premium to the employees on a pro-rata cost basis. Despite the adoption of the conventional multi-tier co-payment schedule, employers are still faced with fifteen to twenty percent premium increases annually that they have to reconcile.

In order to administrate services in processing and analyzing prescription claims of employees/beneficiaries for pharmacy benefits offered under, for example, a multi-tier pharmaceutical benefits structure, pharmacy benefit companies (PBMs) have emerged. The PBM was designed to also negotiate manufacturer rebates and/or pharmacy discounts on behalf of their clients, for example, the insurers that sponsor pharmaceutical benefits, such that the cost of providing the pharmaceutical benefits is maintained low. Although useful, PBMs have been identified as one potential contributor to the continued increase in the costs of pharmaceuticals.

PBMs were designed to provide services to improve the administration of, and thereby reduce the cost of, pharmaceutical benefits for insurers that sponsor those benefits, however, the cost associated with providing pharmaceutical benefits and the cost of a pharmaceutical at the point of sale has continued to increase.

The increased cost can be attributed, in part, to PBMs who do not pass on one hundred percent of pharmacy rebates, negotiated pharmacy discounts and/or manufacturer discounts to the insurance carrier, employer, and/or employee/beneficiary, whose costs increase when there are increases in the costs of pharmaceuticals.

PBMs may also inflate drug costs by only making more expensive drugs available, in which they have a more favorable rebate arrangement with a manufacturer, available to an employee/beneficiary. Drug manufacturers benefit by making the sale, but the parties responsible for paying for the cost of the pharmaceutical, which may be the insurer, the employer, the employee/beneficiary, or any combination of these, do not benefit because a more expensive drug is utilized.

Some pharmaceutical benefits structures require the employer to not only pay a premium to the insurer for the pharmaceutical benefits, but also a portion of the cost of the pharmaceutical beyond, for example, the employee's co-payment. Thus, when more expensive drugs are designated, the employer's contribution to the cost of the pharmaceutical also increases.

As a result employers have considered eliminating pharmaceutical benefits altogether or adopting a "defined contribution" benefits design/structure. A defined contribution benefits structure is one in which the employer puts a limit on its cost, and accordingly, can predetermine at least some, if not all, of its cost of providing the pharmaceutical benefits.

For example, the insurer may charge a forty-dollar premium per employee/beneficiary for the pharmacy benefits. With a defined contribution structure, the employer will determine how much the employer will contribute to the premium. The employer may only assume responsibility for twenty dollars of the forty dollars, and leave the employee/beneficiary responsible for the remainder.

Accordingly, if the premium increases twenty percent the next year to forty-eight dollars, the employer can still choose to contribute twenty dollars to the premium, and impose the eight-dollar increase upon the employee/beneficiary. With the defined contribution benefit structure, the employer is in control of its level of contribution to the pharmaceutical benefits.

A disadvantage, especially in tough economic climates when, for example, unemployment is high and spending is low, of the elimination of pharmaceutical benefits or the transfer of increased costs to the employee/beneficiary may reduce access to needed prescription drugs. This results in poorer health conditions for employees/beneficiaries who cannot afford the pharmaceuticals.

Also, in tough economic climates, where there may be high unemployment rates, the number of people without health insurance also typically increases. As a result, these uninsured people may seek assistance from the government. If the government finds that the cost of financing prescriptions for these uninsured becomes too costly, the government may seek solutions, such as discount card programs and price controls for pharmaceuticals. The discounts and price controls may limit the profits of pharmaceutical manufacturers.

Further, if the pharmaceutical benefits are eliminated by the employer, or if the defined cost benefit structure is adopted by the employer, the employer may not be able to attract or retain employees who may disfavor employment opportunities where there are no pharmaceutical benefits or where increased premium costs are passed on to the employee.

Accordingly, it would be desirable to provide a pharmaceutical benefits design structure that supports affordable health care. It would also be desirable to provide a pharmaceutical benefits design structure that offers quality and affordable pharmaceuticals, to for example, an employee/beneficiary.

Furthermore, it would be desirable to provide a pharmaceutical benefits design structure that passes the advantages of pharmacy discounts and/or manufacturer rebates to the employee/beneficiary, employer and/or insurer.

It would also be desirable to provide a pharmaceutical benefits design structure that limits the employer's cost to provide the pharmaceutical benefits, while providing affordable pharmaceuticals to the employee/beneficiary.

It would also be desirable to provide a pharmaceutical benefits design structure where the beneficiary makes the choice of drug decision rather than the PBM.

SUMMARY OF THE INVENTION

In one aspect of the present invention, a method for calculating a subscriber pharmaceutical cost that incorporates a discount is disclosed that includes, receiving a first discount amount from a pharmaceutical manufacturer at a PBM system for a pharmaceutical, reducing a discount basis for the pharmaceutical utilizing the received discount amount, computing a subscriber cost utilizing the reduced discount basis and transmitting the discount basis to a pharmaceutical dispenser for computing a subscriber cost.

In another aspect of the present invention, a method of providing a pharmaceutical discount to a subscriber at a point of sale is provided that includes, receiving a pharmaceutical cost amount from a PBM at a pharmacy dispenser system, said pharmaceutical cost amount comprising a discount amount from a manufacturer, and transmitting the pharmaceutical cost amount to a subscriber.

In another aspect of the present invention, a method of providing a pharmaceutical cost is provided that includes, receiving a pharmaceutical cost amount from a PBM at an employer system, said pharmaceutical cost amount comprising a discount amount from a manufacturer, and transmitting the pharmaceutical cost amount to a subscriber. The pharmaceutical cost amount may include a discount amount from a pharmaceutical manufacturer. The methods described herein, and in accordance with the present invention, may be embodied in a computer system and/or may be a part of one or more programs that are stored on a computer readable medium.

In another aspect of the present invention, a system for passing a pharmaceutical discount to a subscriber of a pharmaceutical benefit is provided that includes, a pharmacy benefit management system, and a first pharmacy device coupled to the pharmacy benefit management system, wherein pharmaceutical discount data is communicated between the pharmacy benefit management system and the first pharmacy device, and wherein the pharmacy benefit management system determines a subscriber pharmaceutical discount cost that includes one hundred percent of the pharmaceutical discount data.

In yet another aspect of the present invention, a software program for computing a pharmaceutical cost is provided that includes, receiving a discount amount from a pharmaceutical manufacturer into a database of a PBM system, and reducing the pharmaceutical cost by the discount amount.

There has thus been outlined, rather broadly, the more important features of the invention in order that the detailed description thereof that follows may be better understood, and in order that the present contribution to the art may be better appreciated. There are, of course, additional features of the invention that will be described below and which will from the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE FIGURES

FIG. 4 illustrates the tiers in a multi-tier co-payment pharmaceutical benefits structure in accordance with a preferred embodiment of the present invention.

FIG. 5 is an exemplary database of information utilized in the method of the present invention.

DETAILED DESCRIPTION OF THE PREFERRED EMBODIMENTS OF THE INVENTION

Figure 1:
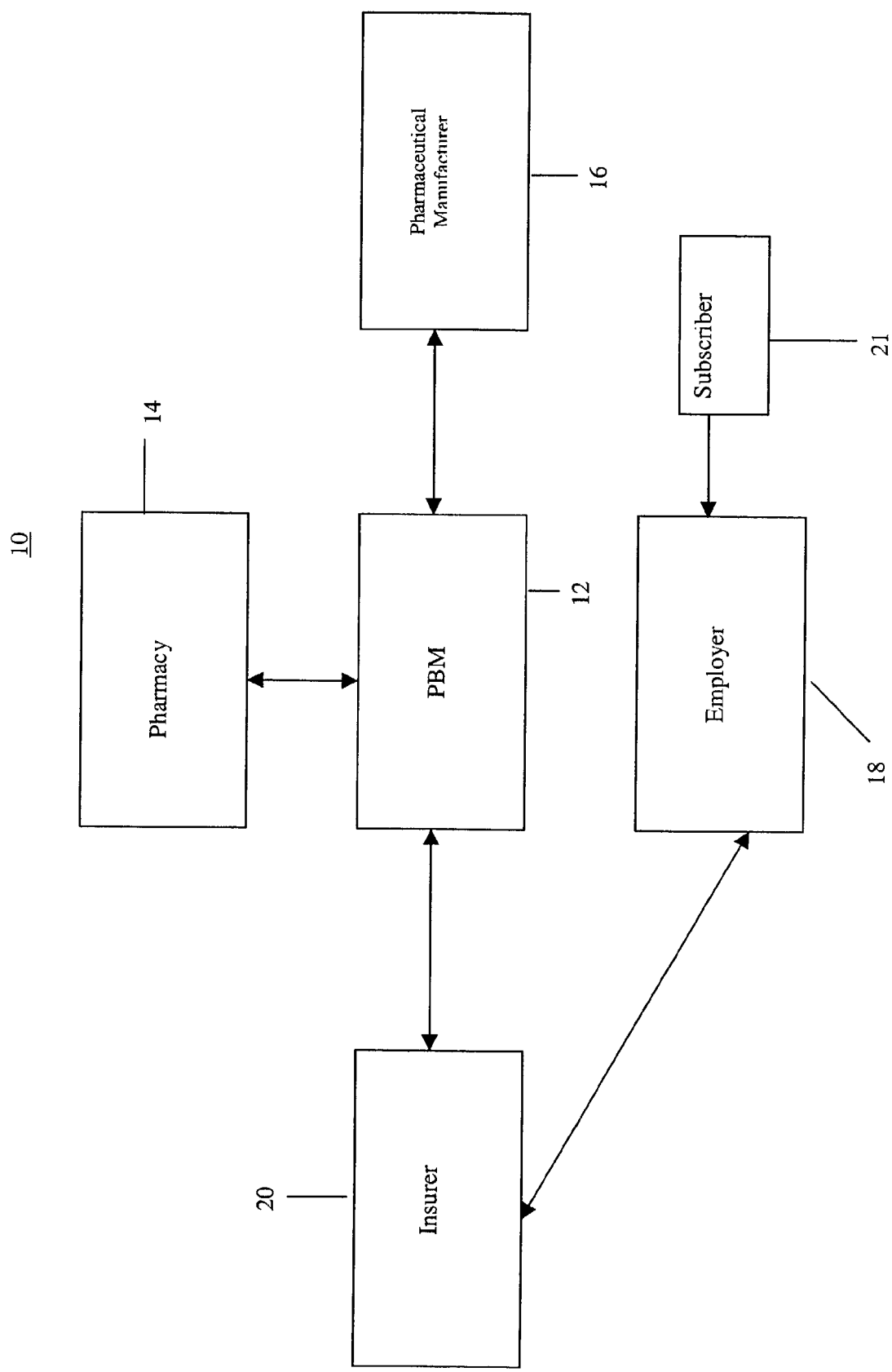
FIG. 1 is a block diagram of the parties involved in the method for calculating and passing rebates and/or discounts to subscribers of pharmaceutical benefits at the point of sale in accordance with a preferred embodiment of the present invention.

Referring now to the figures, in FIG. 1 there is shown a block diagram of the parties 10 involved in determining a pharmaceutical cost utilizing the method of the present invention wherein rebates and/or discounts are passed on to subscribers at the point of sale.

Shown in FIG. 1, is a PBM 12, a pharmaceutical dispenser such as a pharmacy 14, a pharmaceutical manufacturer 16, an employer 18, and an insurer 20. The insurer 20 sponsors the pharmaceutical benefits, to which a party, for example an employer 18, subscribes, to provide assistance to a subscriber 21. A subscriber 21 may be the employer, an employee, a beneficiary of the employee and/or any other individual that obtains pharmaceutical benefits.

The pharmaceutical manufacture 16 offers rebates to the PBM 12 as an incentive for the PBM 12 to make its pharmaceutical available for use by a beneficiary who needs to fill a prescription. It will be readily understood by one of ordinary skill in the art that the rebate may be offered through a distributor that distributes the pharmaceuticals produced by the manufacture 16. For purposes of describing the present invention, a pharmaceutical manufacturer 16 may also refer to a pharmaceutical distributor.

The PBM 12 obtains discounts on pharmaceuticals from the pharmacy 14. In exchange, the PBM 12 identifies the pharmacy 14 to a subscriber 21 as a pharmacy where the prescription benefit will be accepted. A subscriber's 21 benefit may not be accepted at all pharmacies. As a result, the subscriber 21 benefits from the discount pharmaceutical provided by the pharmacy 14, and the pharmacy 14 benefits from the sale of the pharmaceutical to the subscriber 21. The pharmacy 14 may be part of a network of pharmacies that collectively agree to provide discounts on pharmaceuticals to subscribers 21.

Figure 2:
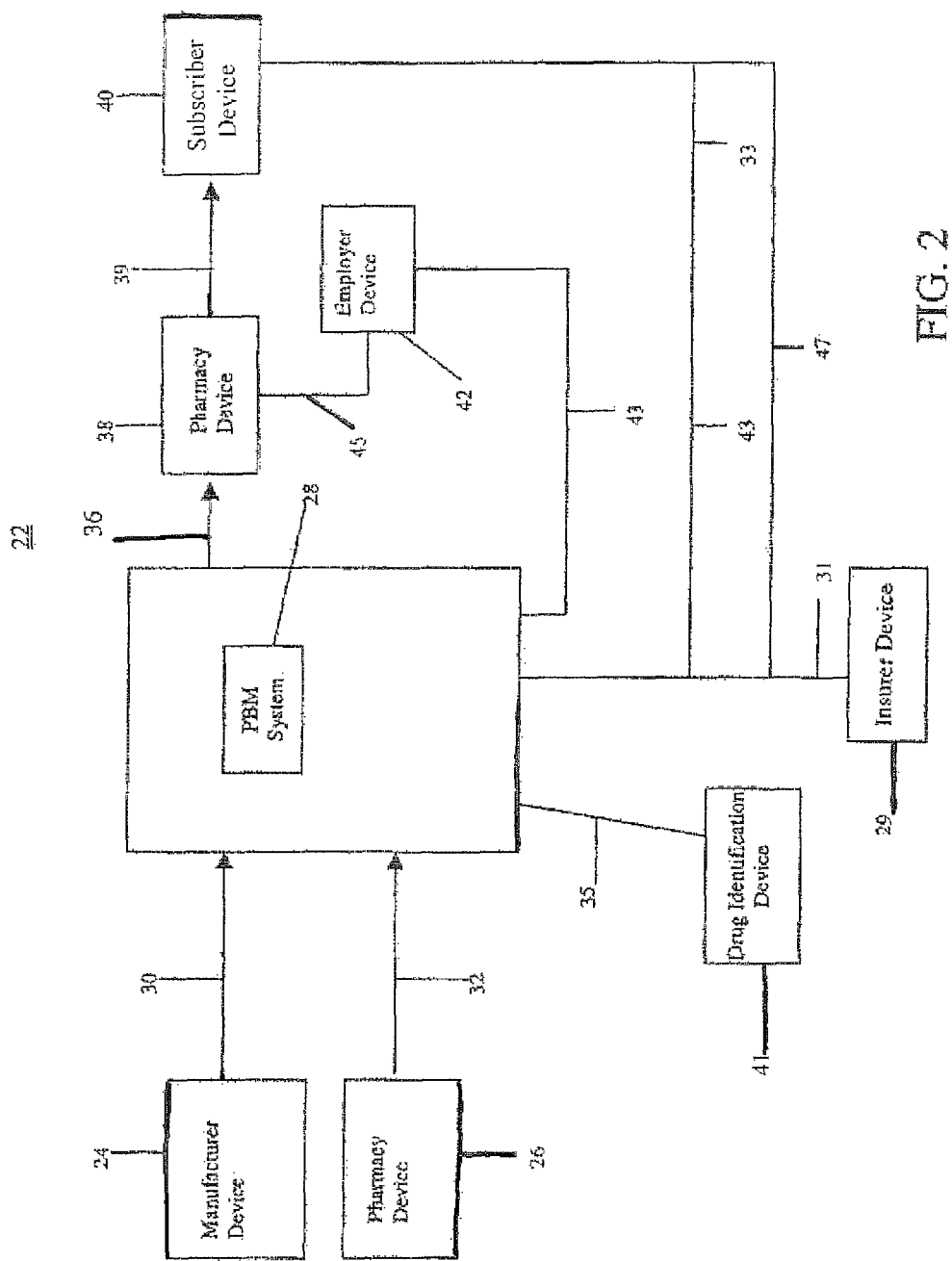
FIG. 2 is a block diagram of a system for calculating and passing rebates and/or discounts to subscribers of pharmaceutical benefits at the point of sale in accordance with a preferred embodiment of the present invention.

The present invention consists of a novel system and method for operating a PBM 12 to allow all discounts and/or rebates to pass directly to a subscriber 21. Shown in FIG. 2, is a novel system 22, for calculating and passing rebates and/or discounts to a subscriber 21 of pharmaceutical benefits at the point of sale. The system 22 includes a manufacturer device 24 and/or pharmacy device 26 that are coupled to a PBM system 28, and utilized to transmit discount amounts/percentages and/or rebate amounts/percentages to the PBM system 28. In an exemplary embodiment of the present invention, the PBM system 28 is coupled, connected, linked, and/or networked to a system/device 29 maintained by the insurer, via an electrical connection/communication line 31, and/or to a system/device 42 maintained by the employer, via communication 33.

Accordingly via a connection 31, 33 to the PBM system 28, the insurer device 29 and/or employer device 42 may also output pharmaceutical manufacturer and/or cost data to a subscriber 21. Thus, a subscriber 21 based on the pharmaceutical manufacturer and/or cost data, may independently select the pharmaceutical that will be utilized to fill his prescription. It should be understood by one of ordinary skill in the art that the term "discount" also describes rebates.

In an exemplary embodiment of the present invention, the manufacturer and/or pharmacy 14 devices 24, 26 are coupled to the PBM system 28, which calculates the cost of the pharmaceutical to the subscriber 21 at the point of sale, for example, electronically via communication lines 30, 32 and/or via a wireless connection, to a the PBM system 28.

In an exemplary embodiment of the present invention, a drug identification device/system 41 is coupled to the PBM system 28 via a communication line 35. The drug identification system 41 maintains for example, a list of the pharmaceuticals, along with price/cost data that is associated with each pharmaceutical. The drug identification device 41, the pharmacy device 26, 38, and/or manufacturer device 24 may transmit, for example, pharmaceutical manufacturer/cost data to the PBM system 28, for example, weekly, to update, the pharmaceutical/manufacturer/cost data.

The PBM system 28 receives the rebates and/or discounts and subtracts the discounts and/or rebates from a discount basis, which may be, for example, an original price of the pharmaceutical, the average wholesale price, or the wholesale acquisition cost. The discount basis utilized by a pharmaceutical dispenser may differ from the discount basis utilized by the pharmaceutical manufacturer. The PBM system 28 calculates and outputs what the cost of the pharmaceutical will be to the subscriber 21 at the point of sale.

The subscriber pharmaceutical cost data is transmitted, via an electrical connection 36, to a second pharmacy device 38 that is coupled to the PBM system 28. However, the pharmacy device 26 may receive the subscriber pharmaceutical cost data. In an exemplary embodiment of the present invention, the pharmacy device 38 transmits, via an electrical connection 39, the subscriber pharmaceutical cost data to a subscriber device 40.

The subscriber device 40 may be an electronic/communication system, for example a processing device, such as a computer, an intranet system/device, an Internet system/device, a cellular telephone and/or any personal communication device that allows a subscriber 21 to receive the subscriber pharmaceutical manufacturer/cost data from the pharmacy device 38. The subscriber device 40 may receive the subscriber pharmaceutical manufacturer/cost data from the PBM system 28 directly, via an electrical connection 47.

Alternatively, the subscriber device 40 may be coupled to a device/system for example, the insurer device 29 and/or employer device 42 that receives pharmaceutical manufacturer/cost data from the PBM system 28 via its connection to the PBM system 28. Accordingly, by utilizing the subscriber device 40, a subscriber 21 may access pharmaceutical manufacturer/cost data, and decide, based on the brand and/or cost of the pharmaceutical, which pharmaceutical he would like a pharmacist to utilize when filling his prescription. In another exemplary embodiment of the present invention, the subscriber 21 may receive the pharmaceutical manufacturer/cost data through the mail.

In the same or another exemplary embodiment of the present invention, the employer may be responsible for the payment of a part or all of the pharmaceutical cost. Accordingly, the employer device 42 is coupled to the PBM system 28 via an electrical connection 43, and/or the pharmacy device 38 via an electrical connection 45, to receive the pharmaceutical cost data.

In an exemplary embodiment of the present invention, the electrical connections that couple the pharmacy devices 26, 38, the manufacturer device 24, the employer device 42 and/or the subscriber device 40 to the PBM system 28 and/or to each other electronically are, for example, wireline or wireless connections.

Figure 3A:
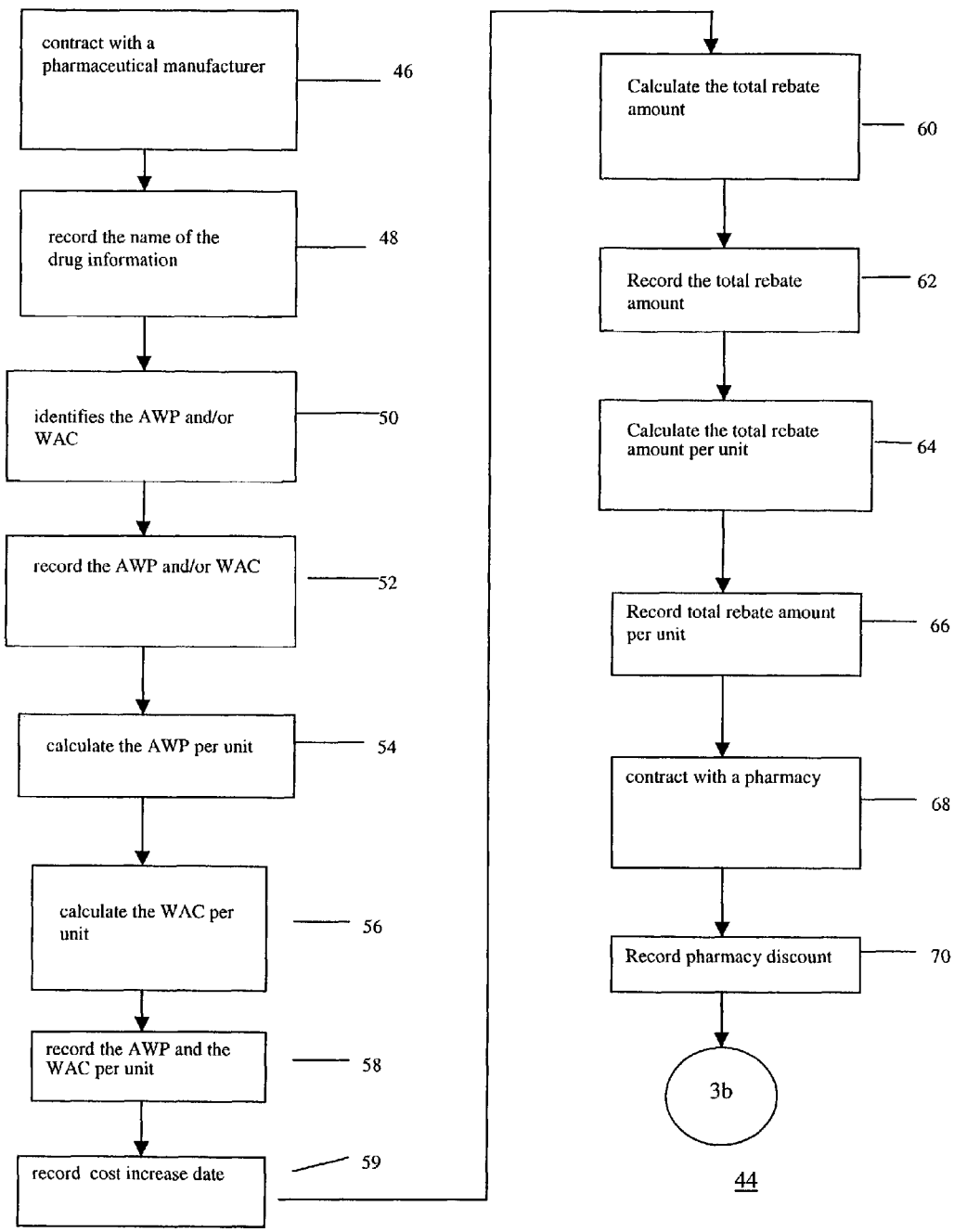
FIGS. 3*a*-3*c* are flow charts of a method for calculating and passing rebates and/or discounts to subscribers of pharmaceutical benefits at the point of sale in accordance with a preferred embodiment of the present invention.
Figure 3B:
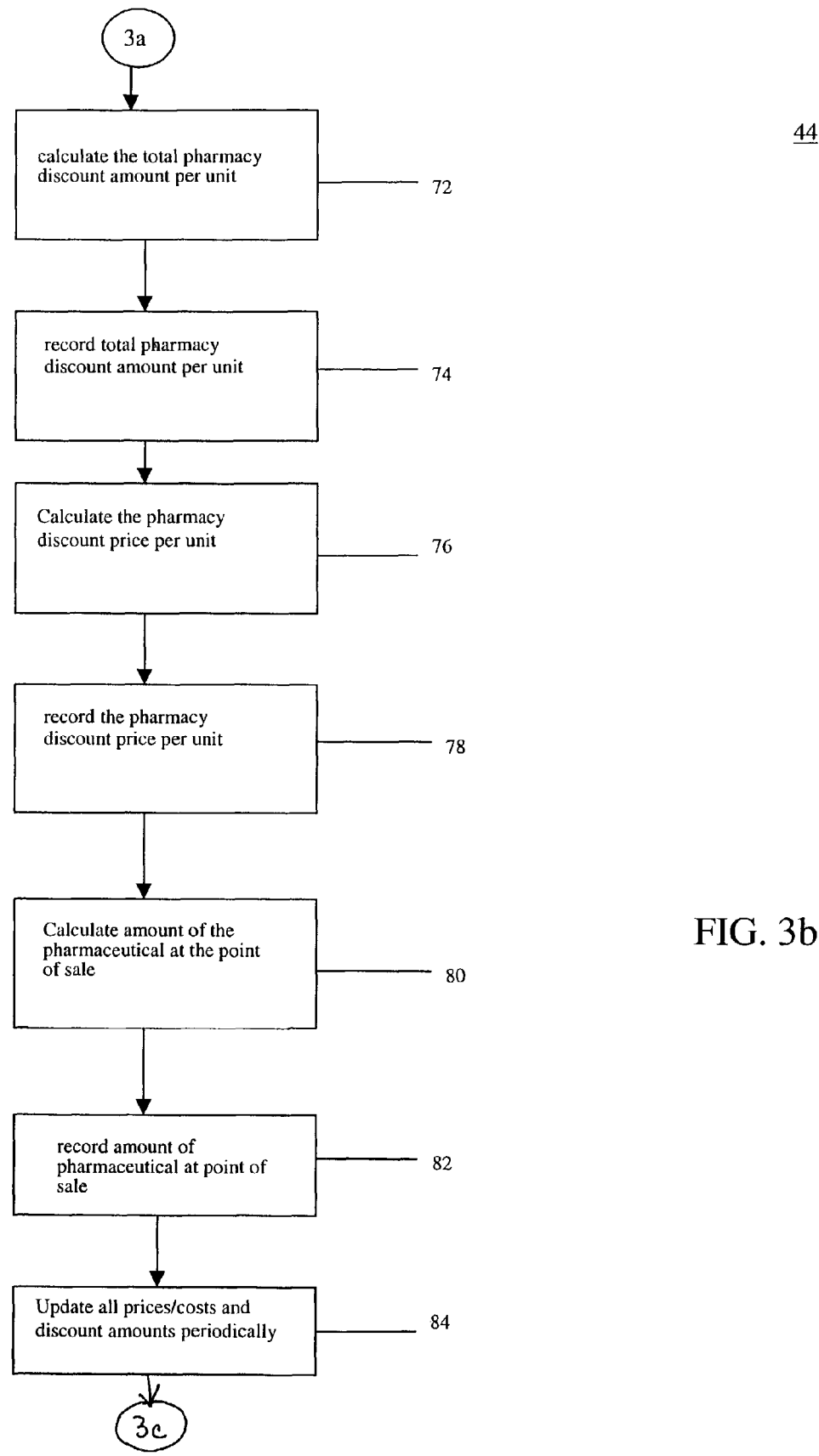
Figure 3C:
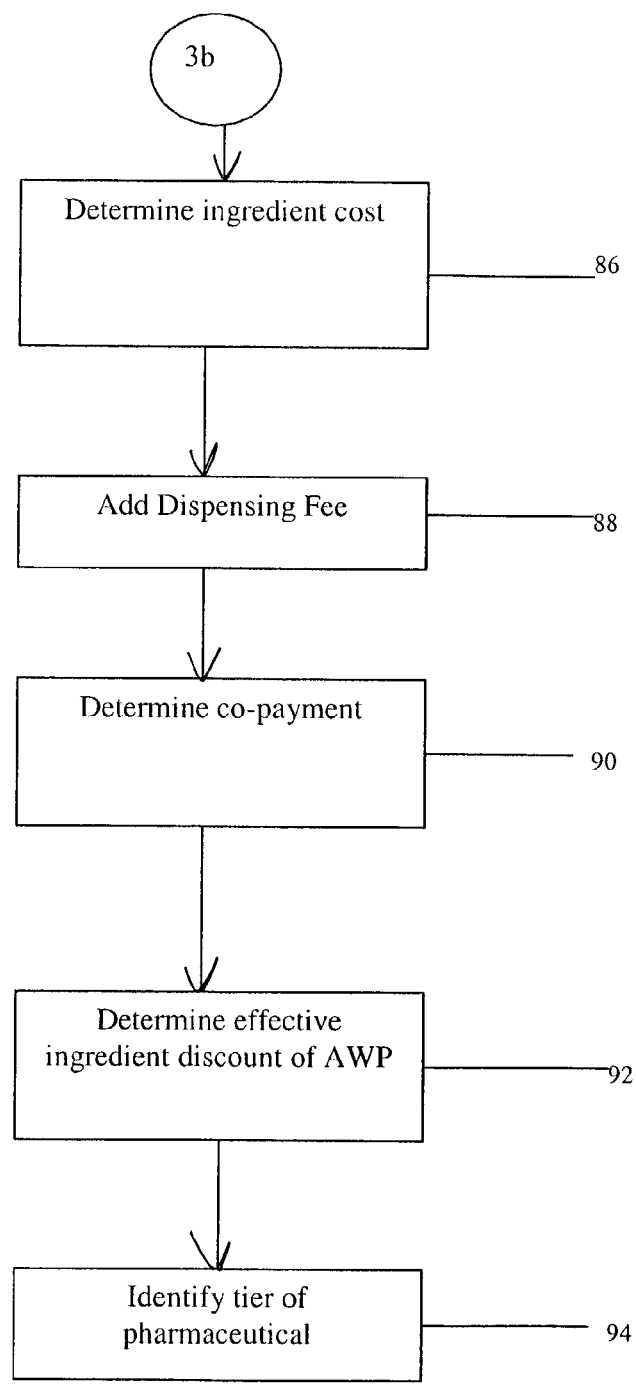

FIGS. 3a-3c is a flow chart illustrating a preferred embodiment of the new method 44, in accordance with the present invention, for calculating the cost of a pharmaceutical to a subscriber at the point of sale. In the method of the present invention, the PBM 12 contracts with a pharmaceutical manufacturer 16 to provide a rebate for specific pharmaceuticals 46. Each contract with a manufacturer 16 will specify each pharmaceutical for which the manufacturer 16 offers a rebate, along with the corresponding National Drug Code (NDC), and the rebate percentage amount.

A National Drug Code is a standard identifier for referencing a pharmaceutical that is allocated to each new pharmaceutical produced by a manufacturer. The National Drug Code includes a sequence of numbers that are used to identify a specific pharmaceutical with the manufacturer (product labeler) 16 of the pharmaceutical. In some instances, the specific pharmaceutical may be identified in connection with the distributor of the pharmaceutical.

The National Drug Code is also composed of an embedded data element, for example, a number that represents the package size. The package size is, for example, the number of units, by weight or volume, which form a trade package.

For example, for a solid pharmaceutical, such as a tablet, the package size of the tablet is represented by units of measurements, such as grams. A package size of a liquid pharmaceutical may be represented in units of milliliters. For pharmaceuticals that are kits, i.e., assemblies of one or more components, the package size is typically referred to in denominations of one where one kit represents one unit.

Each drug under contract is also associated with a rebate percentage. The rebate percentage is a percentage of the cost of the drug that the manufacturer offers as a rebate for the purchase of the drug.

The PBM 12 records and/or stores, for each pharmaceutical under contract, the pharmaceutical name, the pharmaceutical NDC, and the package size 48. In an exemplary embodiment of the present invention, the PBM 12 also records and/or stores the name and NDC of pharmaceuticals that are not under contract.

Each of the pharmaceuticals is associated with a price/cost, representing how much each of the pharmaceuticals would cost a subscriber before any discounts, rebates, and/or co-payments are applied 50. For example, each of the pharmaceuticals is associated with its corresponding average wholesale price (AWP) and/or its corresponding wholesale acquisition cost (WAC). The average wholesale price is an amount that represents the cost of the product plus a mark-up.

The wholesale acquisition cost is the price paid by a wholesaler to the pharmaceutical manufacturer 16 to purchase a specific pharmaceutical, and does not include special deals offered to the wholesaler by the manufacturer 16.

The average wholesale price is determined by surveying national wholesalers to ascertain their price and a suggested mark-up for a new pharmaceutical, or by confirming that the price and mark-up previously supplied is current. The resulting average wholesale price for a pharmaceutical represents the average of the prices charged by the national drug wholesalers for a given product. The average wholesale price is an industry benchmark that is developed independently by entities, such as FIRST DATA BANK® and MEDISPAN®, that specifically monitor the pricing of pharmaceuticals.

Entities, such as FIRST DATA BANK® and MEDISPAN® maintain drug identification systems and/or files that contain a list of pharmaceuticals, along with the most recent prices/costs, and have systems that store, for example, the AWP and WAC for each pharmaceutical, and update the respective pharmaceutical price/cost data, for example, on a weekly basis.

The PBM 12 records and/or stores the average wholesale price and/or wholesale acquisition cost 52. in an exemplary embodiment of the present invention, the PBM 12 imports the AWP and/or WAC information, for each pharmaceutical, via, for example, a network, a disk, the Internet, or an intranet, and downloads the pharmaceutical cost data onto PBM 28 or into a file or computer program of the PBM system 28, for example a database, such as a Microsoft Excel® spreadsheet, that is maintained by the PBM 12. In another exemplary embodiment of the present invention, the PBM 12 maintains the drug identification system of pharmaceutical cost data.

The PBM 12 determines the average wholesale price per unit 54. The average wholesale price per unit is determined by dividing the average wholesale price by the package size, i.e., (AWP/package size). Similarly, the wholesale acquisition cost per unit is determined 56 by dividing the wholesale acquisition cost by the package size, i.e., (WAC/package size).

The average wholesale price per unit and the wholesale acquisition cost per unit are recorded and/or stored by the PBM 58. In a preferred embodiment of the present invention, in step 59, the most recent date of the cost increase, corresponding to, for example, an increase in the average wholesale price and/or the wholesale acquisition cost that the rebate is based upon, is recorded and/or stored.

The total rebate amount is then calculated by multiplying the rebate percentage amount by the price/cost that the rebate is based upon (rebate basis), for example, the average wholesale price or the wholesale acquisition cost, i.e., the total rebate amount equals (rebate percentage×rebate basis) 60. The PBM 12 records and/or stores the total rebate amount 62.

The amount of rebate per unit is determined by dividing the total rebate amount by the package size, i.e., (total rebate amount/package size) 64. The PBM then records and/or stores the total rebate amount per unit 66.

The PBM 12 contracts with an individual pharmacy and/or a network of pharmacies, and each pharmacy 14 provides discounts on specific pharmaceuticals 68. The PBM records the pharmacy discount/amount/percentage 70.

Referring now to FIG. 3b, the total pharmacy discount amount per unit is determined by multiplying the pharmacy discount percentage by the pharmacy discount basis per unit, i.e., (pharmacy discount percentage×pharmacy discount basis per unit) 72. The pharmacy discount basis is the price/cost amount on which the pharmacy discount is based, for example, the average wholesale price or the wholesale acquisition cost. The total pharmacy discount amount is then recorded and/or stored 74.

The pharmacy discount price per unit is determined by subtracting the pharmacy discount amount per unit from the original pharmaceutical cost per unit, which may be, for example, either the average wholesale price per unit or the wholesale acquisition cost per unit 76. For purposes of example, the average wholesale price is utilized as the original pharmaceutical cost. Accordingly, the pharmacy discount price per unit is (AWC per unit−pharmacy discount amount per unit).

Alternatively, the pharmacy discount price is determined by subtracting the pharmacy discount percentage from one hundred percent, and generating a resulting percentage amount, and multiplying the resulting percentage amount by the average wholesale price per unit, i.e., ((100−pharmacy discount percentage)×average wholesale price per unit). The pharmacy discount price per unit is then recorded and/or stored 78.

It should be understood by one of ordinary skill in the art that, although, the pharmacy discount basis and manufacturer rebate basis may be based upon, for example, either the average wholesale price or the wholesale acquisition cost, only one pharmaceutical price/cost, for example, either the average wholesale price or the wholesale acquisition cost, is utilized to determine the pharmacy discount amount.

The subscriber cost of the pharmaceutical per unit at the point of sale, incorporates, for example, one hundred percent of the pharmacy discount and/or the manufacturer rebate, and is determined by subtracting the total rebate amount per unit from the pharmacy discount amount per unit, i.e., (pharmacy discount amount per unit−total rebate amount per unit) 80. The subscriber cost at point of sale is recorded 82.

The average wholesale price, wholesale acquisition cost, rebate amounts, discount amounts, and/or any other prices/costs are updated periodically, for example, on a weekly basis 84.

FIG. 3c illustrates additional items that may be determined and/or calculated by the PBM 12. The ingredient cost is determined by multiplying the subscriber cost per unit by the package size of the drug, i.e., (subscriber cost per unit×package size) 86. This is the cost to fill the prescription or the cost of one trade package.

A dispensing fee is added, for example a three-dollar fee, to the cost of filling the prescription 88. A subscriber co-payment amount is determined by adding the dispensing fee to ingredient cost 90. The effective ingredient discount is determined by dividing the ingredient cost by the pharmaceutical cost, for example ingredient cost/AWP) 92. It should be understood by one of ordinary skill in the art that the steps of method 44 do not have to be performed in the order described above.

Under a multi-tier pharmaceutical benefit structure, the tier of the drug also determines the cost. In a preferred embodiment of the present invention, as shown in FIG. 4, there are five tiers. In order to determine the cost of the pharmaceutical the tier is first determined 94.

A first tier 96 corresponds to generic drugs that have the lowest cost, and typically, are discounted by about fifty percent off of their AWP. A second tier 98 corresponds to primary preferred brand drugs and, typically, are discounted by about thirty percent off of their AWP. A third 100 tier corresponds to preferred brand drugs and, typically, are discounted by about thirty percent off of their AWP. A fourth tier 102 corresponds to selected brand drugs and, typically, are discounted by about twelve to twenty percent off of their AWP.

A fifth tier 104 corresponds to brand drugs that are at least to some extent, not discounted, for example, brand drugs that are not covered by a manufactures discount and/or a pharmacy discount. For example, in an exemplary embodiment of the present invention, where all drug tiers are subject to a pharmacy discount, and all tires except the fifth tier 104 is also subject to a manufacturer discount, the fifth tier 104 corresponds to drugs not covered by a manufacture's discount.

Figure 5:
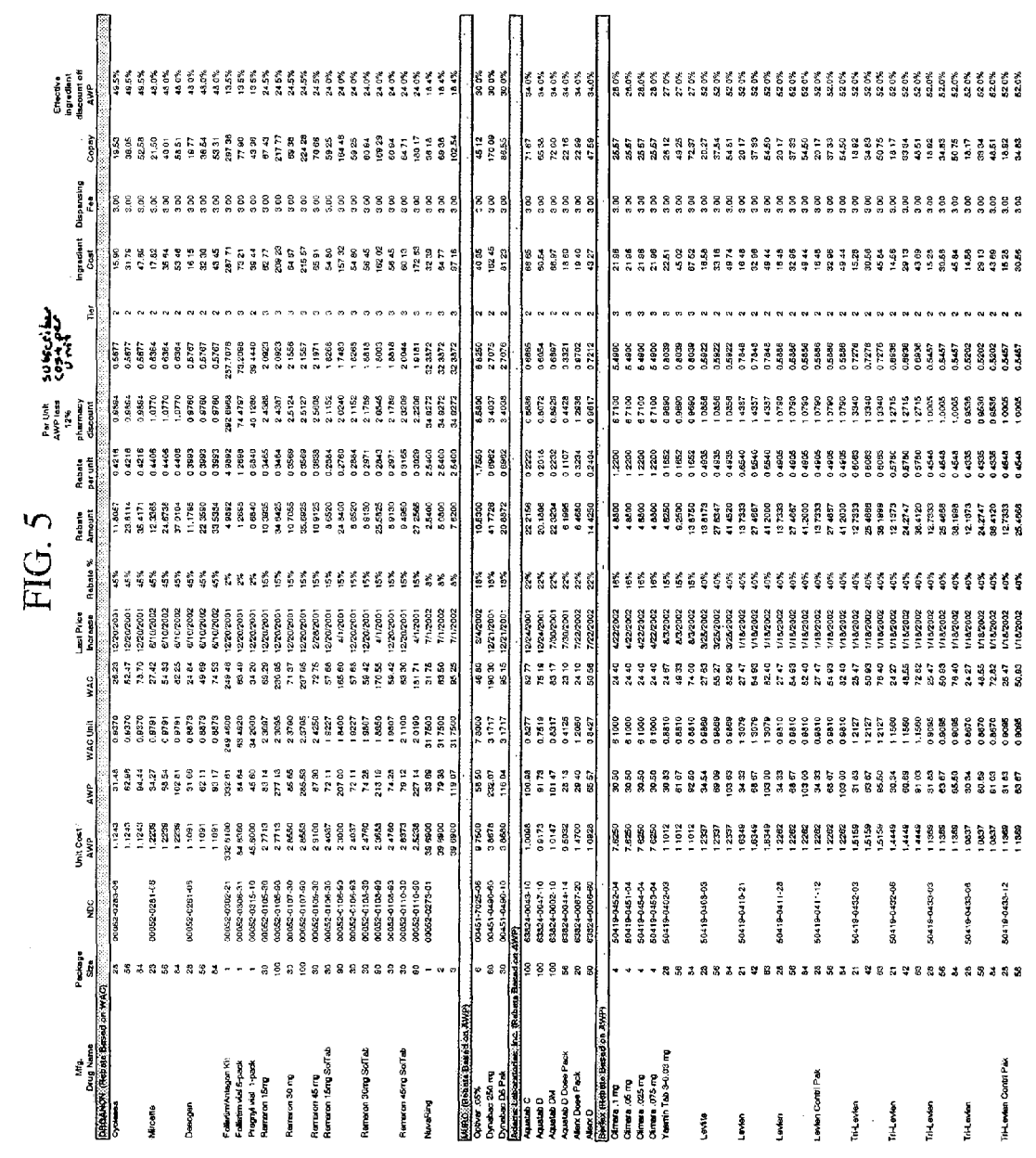

FIG. 5 illustrates a database created using MICROSOFT® EXCEL® spreadsheet that is utilized to calculate, record, and/or store the discount, rebates, and costs associated with pharmaceuticals described above in the method 44 for calculating the cost of a pharmaceutical to a subscriber 21 at the point of sale in accordance with the present invention.

In another exemplary embodiment of the present invention, the method 44 is embodied in a computer readable medium. In another exemplary embodiment of the present invention, the method 44 is embodied in a processing device, for example, an electrically, erasable, programmable, read-only memory device (EEPROM). In yet another exemplary embodiment of the present invention, the method 44 is embodied in a processing system, for example, a computer system.

Thus, according to the method of calculating a subscriber pharmaceutical cost 44, a pharmaceutical manufacturer rebate and/or a pharmacy discount is included in determining the subscriber pharmaceutical cost at the point of sale. The employee/beneficiary benefits because the co-payment reflects the discounts.

The employer benefits when the employer contributes to a portion of the pharmaceutical cost because the discounts are deducted from the remaining balance before determining the employer's balance. Accordingly, the employer directly benefits from the discounts.

In a preferred embodiment of the present invention, the employer will pay the PBM an administrative fee, and thus, the PBM does not benefit from the manufacturer's rebate or the discount offered by the pharmacy. Further, in an exemplary embodiment of the present invention, the PBM system 28 makes the costs of the drugs available to subscribers 21 so that they can make their own drug selection. Accordingly, the opportunity for a PBM 12 to influence the drug choice is reduced.

The PBM 12, as an administrator, combines the employer's contribution, if any, with the pharmaceutical manufacturer rebate and issues a check to the pharmacy for the total amount due for the cost of the pharmaceutical, less the subscriber's 21 co-payment that is paid directly to the pharmacy.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to as falling within the scope of the invention.

What is claimed is:

1. A method performed by an electronic data machine for calculating a pharmaceutical cost for a prescription benefit management (PBM) system, comprising:
   contracting with at least one pharmaceutical manufacturer to obtain a discount basis for said pharmaceutical;
   receiving said discount basis and a pharmaceutical discount from said at least one pharmaceutical manufacturer for said pharmaceutical;
   the electronic data machine calculating a pharmaceutical cost using said pharmaceutical discount and said discount basis for each said pharmaceutical manufacturer;
   storing said pharmaceutical cost and said discount basis and said pharmaceutical discount in a database;
   contracting with at least one pharmacy to obtain a pharmacy discount basis and a pharmacy discount for said pharmaceutical;
   receiving said pharmacy discount basis and a pharmacy discount from said at least one pharmacy for said pharmaceutical;
   calculating a total pharmacy discount cost by using said pharmacy discount and said pharmacy discount basis for each said pharmaceutical manufacturer;
   storing said total pharmacy discount cost and said pharmacy discount basis and said pharmacy discount in said database;
   computing a subscriber cost utilizing said pharmaceutical cost and said total pharmacy discount cost; and
   transmitting said subscriber cost to a pharmaceutical dispenser; and
   adding a dispensing fee to said subscriber cost.

2. The method of claim 1, wherein the discount is represented by a discount percentage.

3. The method of claim 2, wherein the subscriber cost is determined by multiplying the discount percentage by the discount basis to determine a dollar discount amount.

4. The method of claim 3, further comprising subtracting the dollar discount amount from the discount basis to determine the subscriber cost.

5. The method of claim 1, further comprising identifying at least one of an average wholesale price and a wholesale acquisition cost.

6. The method of claim 5, further comprising identifying the package size of a pharmaceutical.

7. The method of claim 6, further comprising dividing the at least one average wholesale price and wholesale price cost by the package size, and generating at least one of an average wholesale acquisition cost per unit and a wholesale cost per unit.

8. The method of claim 6, further comprising determining an ingredient cost amount, wherein the ingredient cost amount is determined by multiplying the subscriber cost by the package size.

9. The method of claim 1, further comprising determining a co-payment.

10. The method of claim 9, further comprising adding a dispensing fee.

11. The method of claim 10, wherein the co-payment includes the dispensing fee.

12. The method of claim 9, further comprising classifying a pharmaceutical by tiers to generate a classification.

13. The method of claim 12, further comprising determining the copayment by the classification of the pharmaceutical.

14. The method of claim 9, wherein there are five tiers.

15. The method of claim 14, wherein a first tier includes generic brands.

16. The method of claim 14, wherein a second tier includes primary preferred brands.

17. The method of claim 14, wherein a third tier includes preferred brands.

18. The method of claim 14, wherein a fourth tier includes selected brands.

19. The method of claim 14, wherein a fifth tier includes non-covered brands.

20. The method of claim 1, further comprising:
   receiving a pharmacy discount amount from a pharmaceutical dispenser at the PBM; and
   reducing the discount basis for the pharmaceutical utilizing the pharmacy discount amount.

21. The method of claim 20, wherein pharmacy discount amounts are received from a plurality of pharmaceutical dispensers.

22. The method of claim 1, wherein the computing is performed at the PBM.

23. The method of claim 1, wherein the computing is performed at a pharmacy.

24. The method of claim 1, wherein the computing is performed by an insurer.

25. The method of claim 1, wherein the computing is performed by an employer.

26. The method of claim 1, wherein the discount basis is an original pharmaceutical cost.

27. The method of claim 1, wherein the discount basis is an average wholesale price.

28. The method of claim 1, wherein the discount basis is the wholesale acquisition cost.

29. The method of claim 1, further comprising updating the discount basis periodically.

30. A method of claim 1, wherein the subscriber cost is computed at a pharmacy.

31. The method of claim 1, wherein the subscriber cost is computed by the insurer.

32. The method of claim 1, wherein the subscriber cost is computed by the employer.

33. A nontransitory computer readable medium storing a program which, when executed by a computer processor, causes the computer to perform a method comprising:
   contracting with at least one pharmaceutical manufacturer to obtain a discount basis for said pharmaceutical;
   receiving said discount basis and a pharmaceutical discount from said at least one pharmaceutical manufacturer for said pharmaceutical;
   calculating a pharmaceutical cost using said pharmaceutical discount and said discount basis for each said pharmaceutical manufacturer;
   storing said pharmaceutical cost and said discount basis and said pharmaceutical discount in a database;
   contracting with at least one pharmacy to obtain a pharmacy discount basis and a pharmacy discount for said pharmaceutical;
   receiving said pharmacy discount basis and a pharmacy discount from said at least one pharmacy for said pharmaceutical;
   calculating a total pharmacy discount cost by using said pharmacy discount and said pharmacy discount basis for each said pharmaceutical manufacturer;
   storing said total pharmacy discount cost and said pharmacy discount basis and said pharmacy discount in said database;
   computing a subscriber cost utilizing said pharmaceutical cost and said total pharmacy discount cost; and
   transmitting said subscriber cost to a pharmaceutical dispenser; and
   adding a dispensing fee to said subscriber cost.

* * * * *